United States Patent
Ren et al.

(10) Patent No.: US 11,468,565 B2
(45) Date of Patent: Oct. 11, 2022

(54) TMB CLASSIFICATION METHOD AND SYSTEM AND TMB ANALYSIS DEVICE BASED ON PATHOLOGICAL IMAGE

(71) Applicant: Institute of Computing Technology, Chinese Academy of Sciences, Beijing (CN)

(72) Inventors: Fei Ren, Beijing (CN); Zhiyong Liu, Beijing (CN); Yudong Liu, Beijing (CN)

(73) Assignee: Institute of Computing Technology, Chinese Academy of Sciences, Beijing (CN)

( * ) Notice: Subject to any disclaimer, the term of this patent is extended or adjusted under 35 U.S.C. 154(b) by 0 days.

(21) Appl. No.: 17/596,127

(22) PCT Filed: Oct. 28, 2019

(86) PCT No.: PCT/CN2019/113582
§ 371 (c)(1),
(2) Date: Dec. 3, 2021

(87) PCT Pub. No.: WO2021/062904
PCT Pub. Date: Apr. 8, 2021

(65) Prior Publication Data
US 2022/0207726 A1 Jun. 30, 2022

(30) Foreign Application Priority Data
Sep. 30, 2019 (CN) .......................... 201910942092.8

(51) Int. Cl.
*G06K 9/00* (2022.01)
*G06T 7/00* (2017.01)
(Continued)

(52) U.S. Cl.
CPC .......... *G06T 7/0012* (2013.01); *A61B 5/7267* (2013.01); *G06V 10/267* (2022.01);
(Continued)

(58) Field of Classification Search
CPC ......... G06T 7/0012; G06T 2207/20021; G06T 2207/20081; G06T 2207/20084;
(Continued)

(56) References Cited

U.S. PATENT DOCUMENTS 10,572,996 B2 * 2/2020 Eurén .................. G06V 20/698
2021/0200987 A1 * 7/2021 Sussman ............ G01N 15/1468

FOREIGN PATENT DOCUMENTS

CN 101983337 A 3/2011
CN 108009400 A * 5/2018
(Continued)

OTHER PUBLICATIONS

Nicolas Coudray et al. "Classification and mutation prediction from non-small cell lung cancer histopathology images using deep learning", Nature Medicine, Sep. 17, 2018, 13 pgs.
(Continued)

*Primary Examiner* — Xin Jia
(74) *Attorney, Agent, or Firm* — Maschoff Brennan (57) ABSTRACT

The invention relates to a TMB classification method and system and a TMB analysis device based on a pathological image, comprising: performing TMB classification and marking and pre-processing on a known pathological image to construct a training set; training a convolutional neural network by means of the training set to construct a classification model; pre-processing a target pathological image of a target case to obtain a plurality of target image blocks; classifying the target image blocks by means of the classification model to acquire an image block TMB classification result of the target case; and acquiring an image TMB
(Continued)

classification result of the target case by means of classification voting using all the image block TMB classification results. The invention further relates to a TMB analysis device based on a pathological image. The TMB classification method of the invention has advantages of accuracy, a low cost and fast rapid.

10 Claims, 7 Drawing Sheets

(51) Int. Cl.
  *G06V 10/82* (2022.01)
  *G06V 10/26* (2022.01)
  *G06V 10/774* (2022.01)
  *G06V 10/764* (2022.01)
  *A61B 5/00* (2006.01)

(52) U.S. Cl.
  CPC .......... *G06V 10/764* (2022.01); *G06V 10/774* (2022.01); *G06V 10/82* (2022.01); *A61B 2576/02* (2013.01); *G06T 2207/20021* (2013.01); *G06T 2207/20081* (2013.01); *G06T 2207/20084* (2013.01); *G06T 2207/30056* (2013.01); *G06T 2207/30096* (2013.01); *G06V 2201/03* (2022.01)

(58) Field of Classification Search
  CPC . G06T 2207/30056; G06T 2207/30096; A61B 5/7267; A61B 2576/02; G06V 10/267; G06V 10/764; G06V 10/774; G06V 10/82; G06V 2201/03
  See application file for complete search history.

(56) References Cited

FOREIGN PATENT DOCUMENTS

| CN | 108009400 A | | 5/2018 |
| CN | 108509991 A | | 9/2018 |
| CN | 108717554 A | | 10/2018 |
| CN | 109628638 A | | 4/2019 |
| CN | 109785903 A | * | 5/2019 |
| CN | 109785903 A | | 5/2019 |
| CN | 109880910 A | | 6/2019 |
| CN | 110245657 A | | 9/2019 |
| CN | 110264462 A | * | 9/2019 |
| CN | 110264462 A | | 9/2019 |
| CN | 110288542 A | | 9/2019 |
| CN | 110866893 | | 3/2020 |

OTHER PUBLICATIONS

Fang Xiao "Study on potential roles of NETs in the pathogenesis of Hashimoto's thyroiditis and underlying mechanisms", Shandong University Doctoral Dissertation, Mar. 25, 2018, 133 pgs.

International Search Report dated Jul. 3, 2020 in PCT Application No. PCT/CN2019/113582, 4 pgs.

First Office Action dated Sep. 20, 2020 in Chinese Application No. 201910942092.8, 21 pgs.

Supplementary Search Report dated Dec. 25, 2020 in Chinese Application No. 201910942092.8.

* cited by examiner

TMB CLASSIFICATION METHOD AND SYSTEM AND TMB ANALYSIS DEVICE BASED ON PATHOLOGICAL IMAGE

CROSS REFERENCE TO RELATED APPLICATIONS

This application is a national application of PCT/CN2019/113582, filed on Sep. 28, 2019. The contents of PCT/CN2019/113582 are all hereby incorporated by reference.

BACKGROUND OF THE INVENTION

1. Field of the Invention

The invention relates to the field of image processing technology, and particularly to a TMB classification method and system and a TMB analysis device based on a pathological image.

2. Related Art

Tumor Mutation Burden (TMB) is an evaluation means of a total number of tumor somatic mutations, and generally refers to the number of non-synonymous mutations per megabase falling into an exon coding region. TMB is an important biomarker in the era of tumor immunotherapy, and therapeutic effect predictive capability of immunotherapy of TMB is not limited to "hot-tumor" (immunogenic tumor) such as NSCLC, melanoma, and the like. However, TMB is a pan-carcinoma biomarker, and has a predictive capability in several tumors including liver cancer. Detection of TMB is an important evaluation means of tumor immunogenicity, and the gold standard method for detection is whole exome sequencing (WES).

The WES cannot be widely applied due to a super high price and an experimental period, and panel sequencing for detecting hundreds of genes (generally, detecting exon coding regions of 1 to 3M genes, while all coding gene regions of human body is about 40M) is the currently common way.

However, since the panel sequencing does not detect all target regions, the obtained TMB is only an approximate value. It is found from a liver cancer data set in The Cancer Genome Atlas (TCGA) through two panel sequencings (IMPACT and FM1) approved by FDA that in the genes directly detected using two panel sequencings, accuracies of predicting exon TMB are 77.8% and 80.7%, respectively, and even after optimization in various ways, the accuracy only reaches about 90%. For example, the Chinese invention "Site Combination, Method, Kit and System for Detecting Tumor Mutation Burden" (application No.: 201910338312.6) provides a site combination, a processing flow and a computing method for detecting TMB based on Panel sequencing, and provides a method for detecting Tumor Mutation Burden to optimize specific sites in a target detection region: excluding high frequent mutation sites associated with generation and development of tumors in Chinese population, and including synonymous mutation, such that consistency of TMB results based on Panel and WES is improved to a certain extent.

Further, even if the panel sequencing, it still faces the problems such as an extra high detection cost, an extra long detection period and dependency of tissue samples. In general cases, it costs several thousands to ten or twenty thousand CNY to obtain TMB by panel sequencing, which forms significant obstacles in widespread application of TMB detection. Moreover, the detection period of obtaining TMB is often 2 to 3 weeks. Finally, obtaining TMB shall have sufficient quantity and sufficient quality of tumor tissue samples, and in actual practice, the case of incapability in obtaining often exists.

Defects in the current panel sequencing are mainly caused by dependency of technological path. Since the gold standard method of TMB is WES, in order to obtain the approximate value of TMB, the detecting region is reduced by the way similar with sampling investigation for prediction. However, due to characteristics of unevenness of distribution of tumor gene somatic mutations, many errors are introduced, causing reduction of accuracy. Meanwhile, the detection method brings disadvantages such as high cost, long period and dependency of tissue samples of technology platform itself of second generation sequencing due to following second generation sequencing of detection technology existing in exome sequencing. Therefore, development of TMB classification acquiring means that is accurate, has a low cost and a fast speed, and is independent of samples except a pathological image has a significant value to research of tumors.

SUMMARY OF THE INVENTION

The invention provides a TMB classification method, comprising: performing TMB classification and marking and pre-processing on a known pathological image to construct a training set; training a convolutional neural network by means of the training set to construct a classification model; pre-processing a target pathological image of a target case to obtain a plurality of target image blocks; classifying the target image blocks by means of the classification model to acquire TMB classification results of image blocks of the target case; and acquiring a TMB classification result of an image of the target case by means of classification voting using the TMB classification results of all the image blocks.

In the TMB classification method of the invention, the step of pre-processing the target pathological image specifically comprises: marking out a target tumor cell region of the target pathological image; cutting out target local images from the target pathological image according to the target tumor cell region; and performing a sliding window segmentation of the target local images, and performing color inversion of target intermediate image blocks obtained by segmentation to obtain the plurality of target image blocks.

In the TMB classification method of the invention, the step of constructing the training set specifically comprises: classifying the known pathological image into a plurality of types according to TMB through at least one classification threshold; marking out all known tumor cell regions of the known pathological image; cutting out a known local image from the known pathological image according to the known tumor cell regions; performing a sliding window segmentation of the known local image, and performing color inversion of intermediate image blocks obtained by segmentation to obtain a plurality of training image blocks; and randomly dividing all the training image blocks to construct training subsets and testing subsets of the training set.

In the TMB classification method of the invention, the convolutional neural network comprises four pairs of convolutional layers and the max pooling layer, one layer of first fully-connected layer, and one layer of second fully-connected layer sequentially; all convolutional layers and the first fully-connected layer use ReLU activation function, and the second fully-connected layer uses Sigmoid activation function; obtaining a plurality of preselected receptive fields by changing a fine grain of convolution kernels of respective convolutional layers of the convolutional neural network, constructing a plurality of corresponding preselected classification models, and acquiring an accuracy and an AUC value of the preselected classification models to use the preselected classification model having the maximum accuracy and the maximum AUC value as the classification model, and the preselected receptive field corresponding to the classification model as an optimal receptive field.

The invention provides a TMB classification system based on a pathological image, comprising: a training set construction module for performing TMB classification and marking and pre-processing on a known pathological image to construct a training set; a classification model construction module for training a convolutional neural network by means of the training set to construct a classification model; a target image pre-processing module for pre-processing a target pathological image of a target case to obtain a plurality of target image blocks; an image block classification module for classifying the target image blocks by means of the classification model to acquire TMB classification results of images blocks of the target case; and an image classification module for acquiring a TMB classification result of an image of the target case by means of classification voting using the TMB classification results of all the images blocks.

In the TMB classification system of the invention, the target image pre-processing module specifically comprises: marking out a target tumor cell region of the target pathological image; cutting out target local images from the target pathological image according to the target tumor cell region; and performing a sliding window segmentation of the target local images, and performing color inversion of target intermediate image blocks obtained by segmentation to obtain the plurality of target image blocks.

In the TMB classification system of the invention, the training set construction module comprises: a TMB marking module for classifying the known pathological image into a plurality of types according to TMB through at least one classification threshold; a local region cutting-out module for marking out all known tumor cell regions of the known pathological image, and cutting out a known local image from the known pathological image according to the known tumor cell regions; a training image block segmentation module for performing a sliding window segmentation of the known local image, and performing color inversion of intermediate image blocks obtained by segmentation to obtain a plurality of training image blocks; and a training set dividing module for randomly dividing all the training image blocks to construct training subsets and testing subsets of the training set.

In the TMB classification system of the invention, the convolutional neural network comprises four pairs of convolutional layers and the max pooling layer, one layer of first fully-connected layer, and one layer of second fully-connected layer sequentially; all convolutional layers and the first fully-connected layer use ReLU activation function, and the second fully-connected layer uses Sigmoid activation function; obtaining a plurality of preselected receptive fields by changing a fine grain of convolution kernels of respective convolutional layers of the convolutional neural network, constructing a plurality of corresponding preselected classification models, and acquiring an accuracy and an AUC value of the preselected classification models to use the preselected classification model having the maximum accuracy and the maximum AUC value as the classification model, and the preselected receptive field corresponding to the classification model as an optimal receptive field.

The invention further provides a readable storage medium stored with an executable instruction for executing the TMB classification method based on a pathological image.

The invention further relates to a TMB analysis device based on a pathological image, comprising a processor and the readable storage medium, the processor calling an executable instruction in the readable storage medium to analyze a target pathological image, and acquire a target classification result of the target pathological image

DETAILED DESCRIPTION

To make objects, technical solutions and advantages of the invention clearer, hereinafter the invention is further explained in details with reference to the accompanying drawings. It shall be understood that the detailed embodiments as described are only to explain the invention, but the invention is not limited thereto.

Based on deep understanding on essence of tumor biology and frontier technology such as genome research technology, and medical image processing, the inventor innovatively provides a new technological path for detecting TMB through a pathological image, and completely breaks dependency of technological path of the current TMB detection means. Based on deep understanding of essence of tumor biology, the invention assumes that as for location of a spatial structure of multiple cells such as tumor cells and immune cells, pathological image features such as morphology of the tumor cells and its microenvironment related cells must have common inherent relation with inherent features of the genome of the tumor cells, and TMB, as the alternative marker of neoantigen, which is the most key point of interaction between the tumor cells and the immune cells, is immunogenicity of the tumor cells, i.e., an important evaluation index of "degree of harm" of an immune system faced by the tumor cells, and also shall be presented in the pathological image. Deep learning is end-to-end learning, and can automatically extract features. New research finds out that deep learning can predict information for driving gene mutation such as epidermal growth factor receptor (EGFR) from the pathological image at a relatively high accuracy, and also can better predict the state of microsatellite instability (MSI) associated with tumor immunology. In the field of image classification, applications of Convolutional Neural Network (CNN) and its derived model are quite wide. In the process of actual development, the invention has experienced several attempts of modeling and training strategies. The inventor finds out that phenomenon of overfitting is very serious after attempting popular models such as AlexNet, VGG and ResNet. Upon analysis, these models are provided to extract features of a nature image, not the pathological image. Relatively, they pay more attention to relation between the main body and its environment in the image, so a feature scale (a receptive field) of these models is quite huge, and each feature in the finally obtained feature map includes extensive information, even global features. However, difference between the problem of predicting high or low of TMB from the pathological image and the problem of classifying the natural image is quite large, because as compared to classification of the natural image (e.g., classification of cat and dog), classification of the pathological image more focuses on tiny details. The inventor uses a collection of local features as a proof of classification to suit for the problem of classification of the pathological image, while relieving the problem of overfitting by narrowing a range of the receptive field, and simplifying the model.

An object of the invention is to solve the defects of low accuracy, high cost, long period and dependency of tissue samples in panel detection technology of TMB detection technology, and the invention provides a method for analyzing a pathological image to perform TMB classification of the pathological image. Through the analysis method of the invention, an accuracy of TMB classification of the pathological image reaches up to 99.7%.

(I) About a Classification Method of a Pathological Image in the Invention

Figure 1:
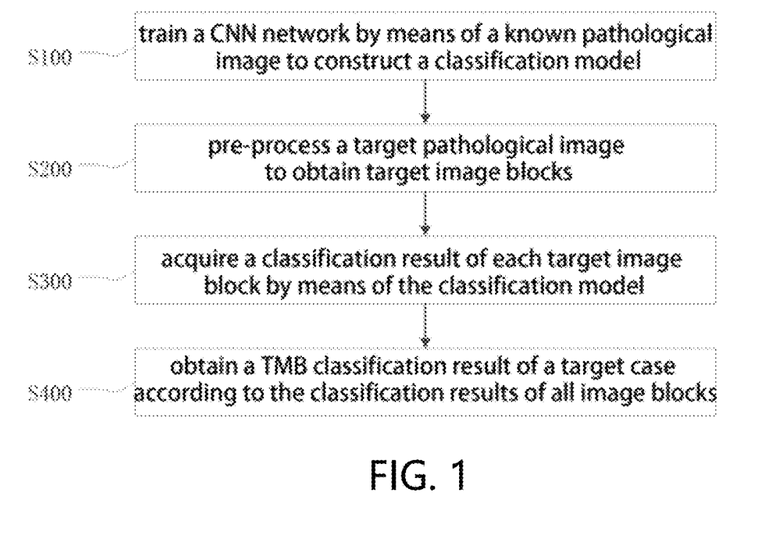
FIG. 1 is a flow diagram of a classification method of a pathological image according to the invention.

FIG. 1 is a flow diagram of a classification method of a pathological image according to the invention. As shown in FIG. 1, the classification method of a pathological image in the invention comprises:

step S100, training a CNN network by means of a known pathological image to construct a classification model; in particular, comprising:

step S110, selecting the known pathological image.

Figure 2:
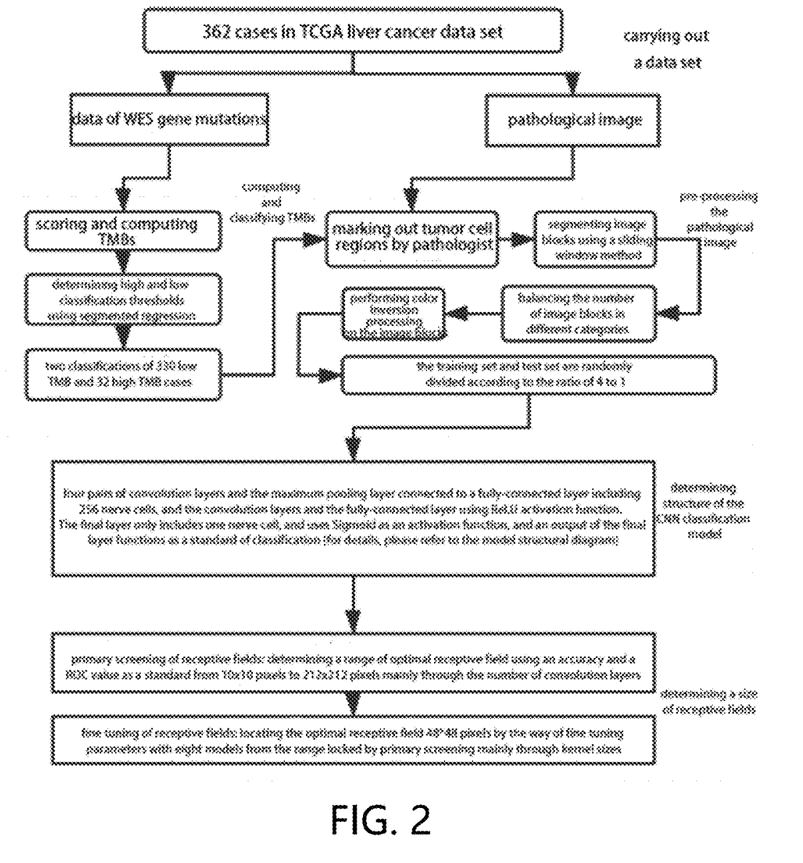
FIG. 2 is a schematic diagram of a process of constructing a classification model in one embodiment of the invention.

The classification model of the invention is an analysis tool of the pathological image of one type of tumors, and training data also uses the pathological image of known cases of the type of tumors. For example, as for a target pathological image of lung cancer cases, the known data of lung cancer pathological image are used as training data of the classification model, and as for gastric cancer cases, the known data of gastric cancer pathological image are used. FIG. 2 is a schematic diagram of a process of constructing a classification model in one embodiment of the invention. As shown in FIG. 2, in the embodiment of the invention, the classification model is constructed by the pathological image of liver cancer cases, so the inventor selects data from liver cancer project of The Cancer Genome Atlas (TCGA) project to construct a training set.

The inventor researches data from the liver cancer project of the TCGA project. TCGA was jointly launched by National Cancer Institute (NCI) and National Human Genome Research Institute (NHGRI) in 2006. Currently, thirty-six cancer types are totally researched. TCGA understands molecular mechanism of the cancers using genome analysis technology based on a large-scale sequencing through extensive cooperation. An object of TCGA is to improve scientific understanding to molecular basis of cancers, enhance capability of diagnosing, treating and preventing the cancers, and finally complete database of genome changes of all cancers. The embodiment searches somatic mutations (single nucleotide variations and small segment insertion loss) from GDC-TCGA liver cancer (LIHC) center using UCSC XENA browser, and uses mutation results obtained from a MUSE analysis method of 362 samples. Only mutations (non-synonymous mutation in an exon region, or located in a shear region) marked with pass filter labels are configured to construct the training set.

step S120, performing classification and marking on the known pathological image.

Before classification of TMB is performed, at least one threshold shall be selected to distinguish high and low of TMB, thereby classifying TMB into two or more types, while currently, liver cancers do not have a TMB threshold in clinical significance. In normal cases, the known pathological image can be classified into two or three types according to TMB, and the known pathological image also can be classified into three or more types according to TMB depending on needs of research, but the invention is not limited thereto. In the following embodiments, unless otherwise specified, taking the known pathological image classified into two types (high TMB and low TMB) according to TMB for example, the TMB classification method of three or more types is the same as the method of two types classifications, and difference is only in the number of TMB thresholds, so the details are not described here.

Figure 3:
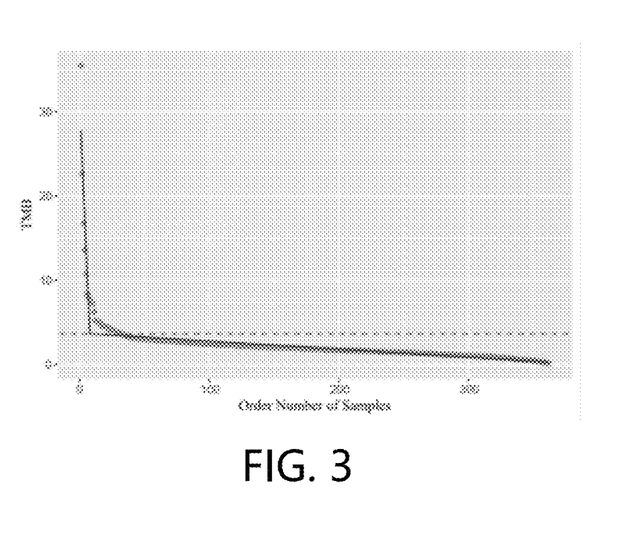
FIG. 3 is a scatter diagram of TMB of a known pathological image in one embodiment of the invention.

In the embodiment of the invention, the threshold is found by finding a inflection point using segmented regression or "fracture rod analysis" to divide the known pathological image into two types according to TMB, in particular, comprising: ranking scores of 362 TMBs in a sequence from large to small, drawing a scatter diagram, fitting scatter points of two straight lines using segmented regression, and finally obtaining the inflection point of the curve. TMB corresponding to the inflection point is a threshold for classifying high TMB and low TMB, and TMB classification of 362 cases is performed using the threshold. FIG. 3 is a scatter diagram of TMB of a known pathological image in one embodiment of the invention. As shown in FIG. 3, performing segmented regression on TMBs corresponding to all known pathological images, and TMB corresponding to the inflection point is about 3.66. A horizontal dotted line passes through the inflection point, and thirty-two points are above the line. Table 1 is a TMB table where thirty-two cases are marked as high TMB cases, and represents that TMBs of the corresponding thirty-two cases are at a high level (marked as high TMB cases), and corresponding pathological images are considered as positive example images; TMBs corresponding to the remaining 330 cases are at a low level (marked as low TMB cases), and corresponding pathological images are considered as negative example images.

TABLE 1

| No. | Case No. | TMB |
| --- | --- | --- |
| 1 | TCGA-UB-A7MB-01A | 35.472 |
| 2 | TCGA-4R-AA8I-01A | 22.667 |

TABLE 1-continued

| No. | Case No. | TMB |
| --- | --- | --- |
| 3 | TCGA-CC-A7IH-01A | 16.750 |
| 4 | TCGA-DD-AAC8-01A | 13.583 |
| 5 | TCGA-DD-A1EE-01A | 10.778 |
| 6 | TCGA-WQ-A9G7-01A | 8.389 |
| 7 | TCGA-DD-AACI-01A | 7.944 |
| 8 | TCGA-DD-A3A9-01A | 7.694 |
| 9 | TCGA-CC-A7IK-01A | 7.333 |
| 10 | TCGA-DD-AACL-01A | 7.222 |
| 11 | TCGA-ED-A7PZ-01A | 6.250 |
| 12 | TCGA-MI-A75G-01A | 5.222 |
| 13 | TCGA-DD-AADF-01A | 5.167 |
| 14 | TCGA-DD-AACQ-01A | 5.111 |
| 15 | TCGA-DD-AAE7-01A | 5.028 |
| 16 | TCGA-G3-A3CK-01A | 4.917 |
| 17 | TCGA-CC-A8HT-01A | 4.583 |
| 18 | TCGA-LG-A6GG-01A | 4.583 |
| 19 | TCGA-DD-AADO-01A | 4.583 |
| 20 | TCGA-CC-A5UD-01A | 4.528 |
| 21 | TCGA-DD-AACT-01A | 4.500 |
| 22 | TCGA-ED-A459-01A | 4.306 |
| 23 | TCGA-RC-A6M6-01A | 4.278 |
| 24 | TCGA-DD-AAEA-01A | 4.139 |
| 25 | TCGA-RC-A6M4-01A | 4.139 |
| 26 | TCGA-DD-AACZ-01A | 4.083 |
| 27 | TCGA-G3-A7M5-01A | 4.000 |
| 28 | TCGA-BC-A10Z-01A | 3.861 |
| 29 | TCGA-CC-A7IE-01A | 3.806 |
| 30 | TCGA-MI-A75I-01A | 3.750 |
| 31 | TCGA-DD-AADM-01A | 3.750 |
| 32 | TCGA-G3-AAV0-01A | 3.667 |

Step S130, pre-processing the known pathological image.

380 whole slide images of 362 liver cancer patients are downloaded from the TCGA-LIHC project using GDC tool, and these cases are in one-to-one correspondence with the cases of TMB data mentioned above.

Step S131, marking out a tumor cell region.

An image having the maximum scan resolution included in a data set is at least 20× (magnification times of an object lens), and 20× field of view is a practice of the doctor for judging benign and malignant of the tumors under the lens, so the invention cuts out several local images with 1712*961 pixels from each 20× image, and the local images only include cancerous areas (tumor cell regions). In the process of cutting the image, twelve section images of twelve cases are excluded due to a poor image quality. Finally, the high TMB cases (positive example images) are totally cut out 470 local images, and the low TMB cases (negative example images) are totally cut out 5162 local images.

Step S132, segmenting all local images to obtain training image blocks.

Figure 4:
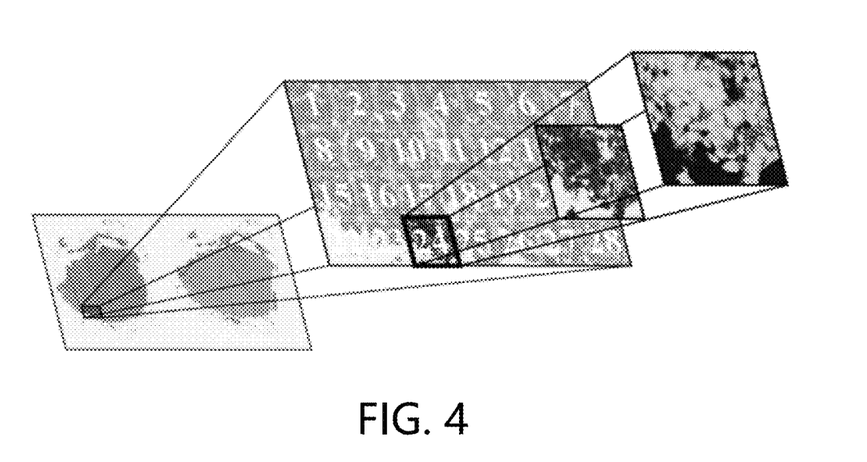
FIG. 4 is a schematic diagram of image block segmentation in one embodiment of the invention.

If the local images are directly configured for training of a deep learning model, the problems of a large resolution and imbalance of classification are faced, and the invention segments the local images into a plurality of image blocks by the way of flexibly adjusting a stride, thereby reducing the resolution and balancing the classification. Segmentation of the image blocks can use multiple ways, such as, threshold segmentation, and region segmentation, and in the embodiment of the invention, the training image blocks are segmented using a sliding window method. FIG. 4 is a schematic diagram of image block segmentation in one embodiment of the invention. As shown in FIG. 4, a size of the sliding window in the embodiment of the invention is 256×256 pixels, and as for the local images of the negative example images, each image is cut into 28 image blocks according to four rows and seven columns. Although the image blocks have few overlapped portions among one another, it has been a scheme with the minimum overlapped area, on the premise of not omitting each pixel. As for the local images of the positive example images, each image is cut into 300 small image blocks according to twelve row and twenty-five columns, such that the local images of all positive example images can be segmented into 141,000 image blocks in 256×256 pixels, and the local images of the negative example images can be segmented into 144,536 image blocks having the same resolution (256×256 pixels). The number of image blocks of the two classifications is approximately the same, thereby solving the problem of imbalance of classification while enhancing data.

Step S133, performing color inversion processing on the training image blocks.

Since some image blocks are located on an edge portion of tumor cell tissue, a blank local area may be included. White color has a relatively high color value in a RGB system, and a color value corresponding to color of cells (especially a cell nucleus) is low. When these image blocks are inputs of the deep learning model, a eigenvalue corresponding to pixel points without the meaning of analysis is approximate to 0, and the pixel points having the meaning of analysis correspond to a higher eigenvalue, thereby facilitating training and analysis of the classification model, so the invention performs color inversion of all image blocks.

Step S134, randomly dividing a training set and a testing set according to a ratio of 4:1;

Step S140, training a convolutional neural network according to the training set and the testing set.

The convolutional neural network (CNN) and its derived model have a wide application in the image classification field. The CNN is a feedforward neural network, and history can be traced to year of 1962. Biologists Hubel and Wiesel found out that cells in cat visual cortex were sensitive to a part of visual inputs, so the concept of receptive field was provided. In 1980, Kunihiko provided a new cognitive accelerator based on local receptive field theory from Hubel and Wiesel. This is the earliest implementation of the CNN network model, and a receptive field is one basic concept of the CNN. What is different from the fully-connected network where features are dependent on whole input, each nerve cell in the convolutional layer establishes connection with nerve cells in the upper receptive field only through a convolution kernel, and the region is a receptive field of the nerve cells. The CNN absorbs idea of local receptive fields, and has advantages of weight sharing and local connection. The CNN can effectively control parameter sizes and computation while ensuring training effect.

After attempting popular models such as, AlexNet, VGG and ResNet, the inventor finds out that phenomenon of overfitting is quite serious. Upon analysis, these models are provided to extract features of a natural image, not the pathological image. Relatively, they pay more attention to relation between the main body and its environment in the image, so a receptive field of these models is quite huge, and each feature in the finally obtained feature map includes extensive information, even global features. For example, the receptive field of pixels in the feature map outputted from pool5 of AlexNet is 195×195 pixels on an input image, the maximum receptive field of VGG16 is 212×212 pixels, and the maximum receptive field of ResNet50 even can reach 483×483 pixels.

However, difference between the problem of predicting high or low of TMB of one case from the pathological image and the problem of classifying the natural image is quite large, because as compared to classification of the natural image (e.g., classification of cat and dog), classification of the pathological image more focuses on tiny details. Therefore, the invention uses a collection of local features as a proof of classification to suit for the problem of classification of the pathological image, while relieving the problem of overfitting by narrowing a range of the receptive field, and simplifying the model.

Figure 5:
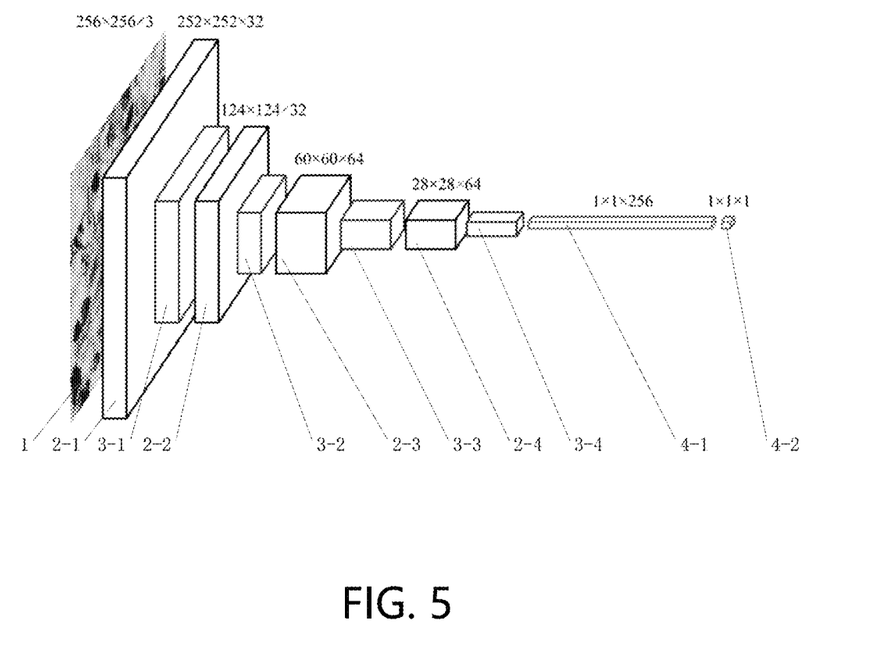
FIG. 5 is a structural diagram of a convolutional neural network in one embodiment of the invention.

The CNN can have various structural forms, but not the CNN in all structural forms can obtain better TMB classification effect. FIG. 5 is a structural diagram of a convolutional neural network in one embodiment of the invention. As shown in FIG. 5, after testing of different hyper-parameters, the invention finally selects to use four pairs of convolutional layers 2-1, 2-2, 2-3, 2-4 and the maximum pooling layers 3-1, 3-2, 3-3, 3-4 sequentially connected to a fully-connected layer 4-1 including 256 nerve cells and a fully-connected layer 4-2 only including one nerve cell, the convolutional layers 2-1, 2-2, 2-3, 2-4 and the fully-connected layer 4-1 use ReLU activation function, and the fully-connected layer 4-2 uses Sigmoid as an activation function. In such way, after processing and analysis on a target image block 1, an output of the fully-connected layer 4-2 functions as a standard of classification.

The embodiment is a preferable embodiment of training the CNN on the known pathological image of the confirmed liver cancer patients acquired from the TCGA-LIHC project, and when training categories of other types or using other training data, the CNN in other structural forms may be used to obtain better classification effect, for example, three pairs of convolutional layers and the maximum pooling layer and one fully-connected layer, or five pairs of convolutional layers and the maximum pooling layer and one fully-connected layer, but the invention is not limited thereto.

Step S150, determining a size of receptive field of the classification model.

In the process of training the CNN network model, the size of receptive field can be controlled by the method of adjusting a depth of the CNN model and adjusting a size of the convolution kernel. However, with change of the depth of the model, the number of parameters of the model is significantly changed, which largely affects training effect (overfitting or underfitting effect may be produced), so the invention controls the receptive field mainly using the method of changing the size of the convolution kernel.

TABLE 2

| Model ID | Kernel Sizes of 4 Convolutional Layers | | | | Receptive Field RF (pixel) |
| --- | --- | --- | --- | --- | --- |
| | Kernel 1 | Kernel 2 | Kernel 3 | Kernel 4 | |
| RF46 | 3 × 3 | 3 × 3 | 3 × 3 | 3 × 3 | 46 × 46 |
| RF48 | 5 × 5 | 3 × 3 | 3 × 3 | 3 × 3 | 48 × 48 |
| RF50 | 3 × 3 | 5 × 5 | 3 × 3 | 3 × 3 | 50 × 50 |
| RF52 | 5 × 5 | 5 × 5 | 3 × 3 | 3 × 3 | 52 × 52 |
| RF54 | 3 × 3 | 3 × 3 | 5 × 5 | 3 × 3 | 54 × 54 |
| RF56 | 5 × 5 | 3 × 3 | 5 × 5 | 3 × 3 | 56 × 56 |
| RF58 | 3 × 3 | 5 × 5 | 5 × 5 | 3 × 3 | 58 × 58 |
| RF60 | 5 × 5 | 5 × 5 | 5 × 5 | 3 × 3 | 60 × 60 |

In the embodiment of the invention, a series of experiments are made, and a suitable range of the receptive field is locked between 46×46 pixels and 60×60 pixels by largely changing the receptive field (from 10×10 pixels to 212×212 pixels). Then, in the case of a fixed number of convolutional layers, different kernel sizes are used within the interval to better fine-grained control the receptive field. Eight models are designed by extracting several kernels of the first three convolution layers in the model to modify from 3×3 to 5×5, as shown in Table 2.

After the eight models are trained using the same data set, accuracies and Area Under Curve (AUC, an area under receiver operating characteristic (ROC) curve) values of the respective models are shown in Table 3. According to experimental results, the model with the best effect is RF48, and an optimal receptive field is 48×48 pixels.

TABLE 3

| Model ID | RF (pixel) | Test Accuracy | Test AUC |
| --- | --- | --- | --- |
| RF46 | 46 × 46 | 0.9232 | 0.9215 |
| RF48 | 48 × 48 | 0.9486 | 0.9488 |
| RF50 | 50 × 50 | 0.9315 | 0.9175 |
| RF52 | 52 × 52 | 0.8765 | 0.8846 |
| RF54 | 54 × 54 | 0.8823 | 0.8804 |
| RF56 | 56 × 56 | 0.8697 | 0.8783 |
| RF58 | 58 × 58 | 0.8754 | 0.8729 |
| RF60 | 60 × 60 | 0.9033 | 0.8700 |

Step S200, pre-processing a target pathological image of a target case to obtain target image blocks;

Pre-processing of the target pathological image is similar with pre-processing of the known pathological image to construct a training set, comprising:

Step S210, marking out a tumor cell region of the target pathological image;

Step S220, cutting out local images with a size of 1712×961 pixels from the target pathological image according to the tumor cell region;

Step S230, segmenting the cut out local images, for example, segmenting in the same manner as constructing the training set, using a sliding window with a size of 256×256, and segmenting 300 image blocks from each target case image in a way of twelve rows and twenty-five columns; segmenting can be performed in other ways, but the invention is not limited thereto;

Step S240, performing color inversion processing on the segmented image blocks;

Step S300, analyzing the target image blocks according to the classification model, and acquiring TMB classification results of image blocks of the target case.

As for each image block, it is classified by means of the classification model to obtain the TMB classification result of the image block of the target case relative to each image block, and determine whether TMB is at a high level or a low level.

Step S400, obtaining a TMB classification result of an image of the target case according to the TMB classification results of all the image blocks.

When all image blocks are classified by means of the classification model, i.e., obtaining the TMB classification result of the image block of the target case relative to all image blocks, the TMB classification result of the image of the target case relative to the target pathological image is obtained according to the TMB classification results of all image blocks. In the embodiment of the invention, the TMB classification result of the target image is obtained by the voting method to vote a TMB level of the target case relative to the target pathological image according to the TMB classification results of the image blocks, and the TMB classification result of the image block having the maximum number of votes is the TMB classification result of the image of the target case.

It shall be understood that a segmented size of the local images, and a size of the sliding window are not limited to fixed pixels as described, but only to clearly explain the method provided in the invention, and the local images also can be segmented, or the sliding window also can be selected by other sizes, but the invention is not limited thereto.

(II) About a TMB Analysis Device Based on a Pathological Image in the Invention

Figure 6:
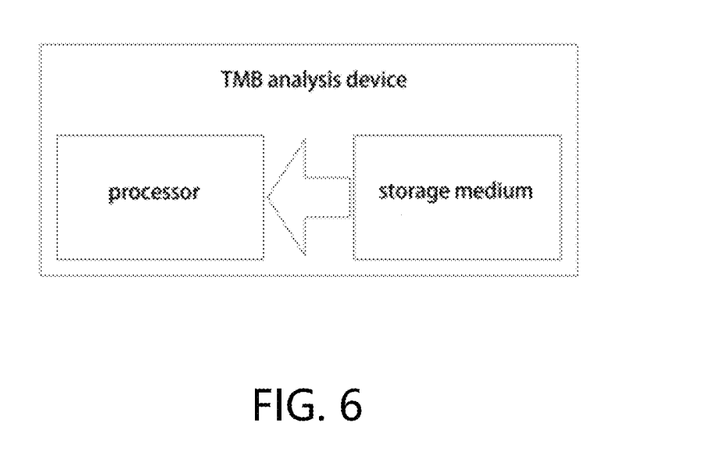
FIG. 6 is a structural diagram of a TMB analysis device based on a pathological image according to the invention.

FIG. 6 is a structural diagram of a TMB analysis device based on a pathological image according to the invention. As shown in FIG. 6, the embodiment of the invention further provides a readable storage medium and a data processing device. The readable storage medium of the invention is stored with an executable instruction, and when the executable instruction is executed by a processor of the data processing device, the TMB classification method based on a pathological image is realized. Those ordinary in the art can understand that all or part of steps in the method can be completed by instructing relevant hardware (e.g., processor, FPGA, ASIC, etc.) through programs, and the programs can be stored in the readable storage medium, such as, read-only memory (ROM), disk or optical disc. All or part of steps in the embodiment also can be implemented by one or more integrated circuits. Correspondingly, the respective modules in the embodiment can be implemented in the form of hardware, for example, realizing corresponding functions through the integrated circuits, and also can be implemented in the form of software functional modules, for example, executing programs/instructions stored in a memory through the processor to realize the corresponding functions. The embodiment of the invention is not limited to a combination of hardware and software in any specific form.

Figure 7A:
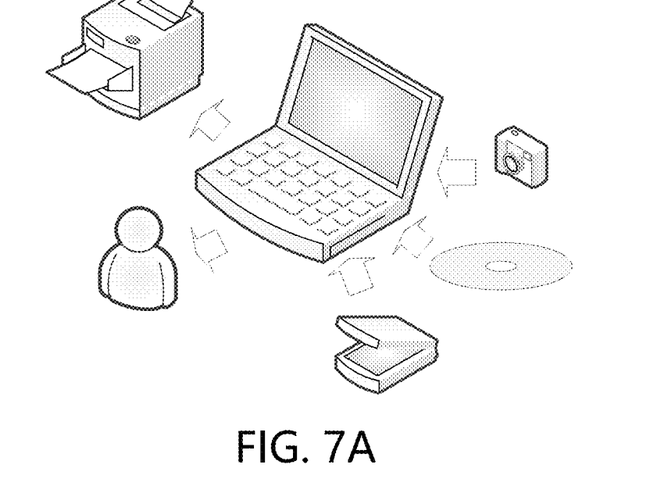
FIGS. 7A, 7B and 7C are schematic diagrams of specific embodiments of a TMB analysis device based on a pathological image according to the invention.

FIGS. 7A, 7B and 7C are schematic diagrams of specific embodiments of a TMB analysis device based on a pathological image according to the invention. The data processing device of the invention can have various specific forms to perform TMB classification based on the pathological image. For example, as shown in FIG. 7A, in the embodiment of the invention, a computer is used as the TMB analysis device, and an input unit of the TMB analysis computer comprises at least one of input devices or interfaces such as a digital camera, a digital webcam, a scanner, a card reader, a drive, and a USB interface, and can convert the known pathological image and the target pathological image to data files and input into the TMB analysis computer, or directly inputting data files of the known pathological image and the target pathological image into the TMB analysis computer. Computer executable instructions for implementing the TMB classification method based on a pathological image in the invention are stored in storage units of the TMB analysis computer, and the processor of the TMB analysis computer calls and executes the computer executable instructions for processing inputted data of the known pathological image and/or data of the target pathological image to generate the classification model or obtain the corresponding TMB classification of the target pathological image. When the TMB classification result is obtained, the TMB classification result based on the target pathological image is outputted to users through an output unit of the TMB analysis computer, such as, a printer or a display.

Figure 7B:
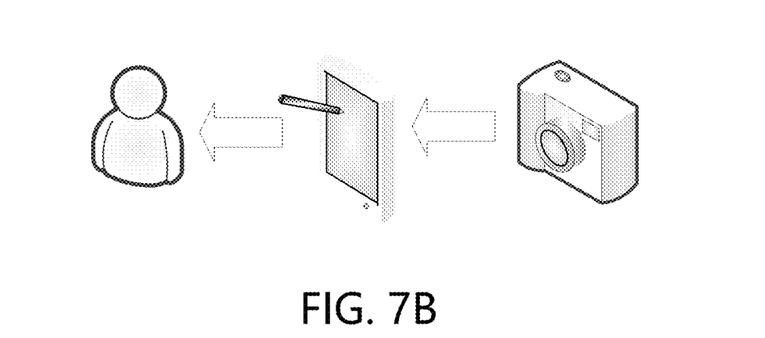
Figure 7C:
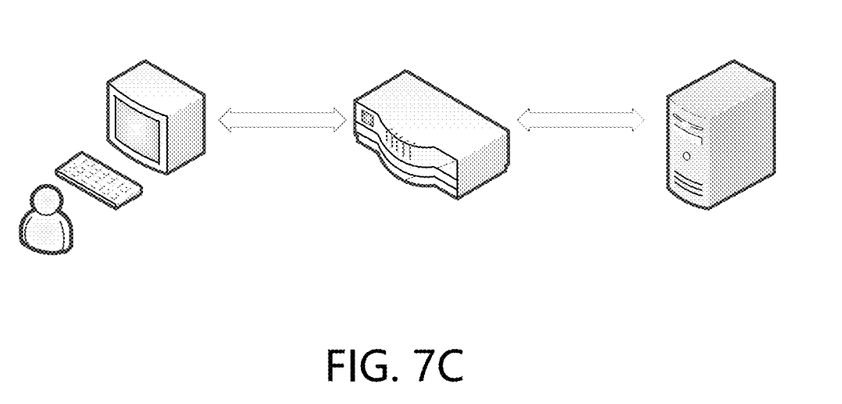

The TMB analysis device of the invention also can be based on the generated classification model, i.e., the TMB analysis device stops constructing the classification model according to the known pathological image, but the constructed classification model is stored in the storage units of the TMB analysis device, except stored with the computer executable instructions for implementing the TMB classification method based on a pathological image in the invention, and the processor of the TMB analysis device calls and executes the computer executable instructions and the classification model, and processes and analyzes the inputted data of the target pathological image to obtain the corresponding TMB classification of the target pathological image. When the TMB classification result is obtained, it is outputted by the output unit of the TMB analysis computer, such that the TMB analysis device can reduce the requirement for processing performance of the processor, and largely simplifies the degree of complexity of the TMB analysis device, or increases portability of the TMB analysis device, or expands range of application of the TMB analysis device. As shown in FIG. 7B, in another embodiment of the invention, a tablet PC is used as the TMB analysis device, such that the target pathological image can be processed conveniently, and mobile terminals such as smart phones also can be used, but the invention is not limited thereto. As shown in FIG. 7C, in yet another embodiment of the invention, a network server is used as the TMB analysis device, such that a network platform can be built, and users shall only input data of the target pathological image at network terminals to obtain TMB classification result of the target pathological image via network devices such as exchanger/gateway through a network server on a local area network (LAN) or a wide area network (WAN).

(III) About Technical Effects of the Classification Method of the Pathological Image in the Invention As can be seen, the classification method of the pathological image in the invention classifies image blocks segmented from the pathological image and the pathological image itself. In practical use, after the receptive field is determined and the model is trained using the pre-processed data set, as for TMB classification of the image blocks, an accuracy of the testing set is 0.9486, and an AUC value is 0.9488 using result of the tenth training period by drawing accuracy, loss and AUC curve. However, as for TMB classification of the pathological image, based on the classification model, 350 known cases are classified and predicted, each pathological image is segmented into 816 image blocks on average, and after the TMB level of each image block of a case is predicted, an overall TMB level of the pathological image of the current case is computed using majority voting method. After experiments are completed, only one prediction in 350 patients is wrong, and belongs to a false negative category, and an accuracy of classification of TMB patient predictions is 0.9971.

Since normal tissue regions of the pathological image are excluded during data pre-processing, the segmented image blocks without normal tissue regions are added into the training set in the process of training the model. To detect predictive capability of the image blocks in the normal tissue regions of the pathological image, the invention also classifies and predicts local images of normal tissues: cutting the collected local images of the normal tissues into 768 blocks for prediction (all labeled as low TMB), so result is that three image blocks are wrongly judged to high TMB, and an accuracy is 0.9961.

(IV) As for Effect Comparison Between the Classification Method of the Pathological Image in the Invention and the Prior Art Since most TMB scores for clinical reference are now obtained by gene panel, panel TMB obtained by such way is an approximate value of TMB obtained by WES TMB. Currently, FDA has approved two gene panels of MSKCC IMPACT468 and FM1. We extract genes of the two panels from the TCGA-LIHC project, and compute TMB scores of these panels.

Figure 8:
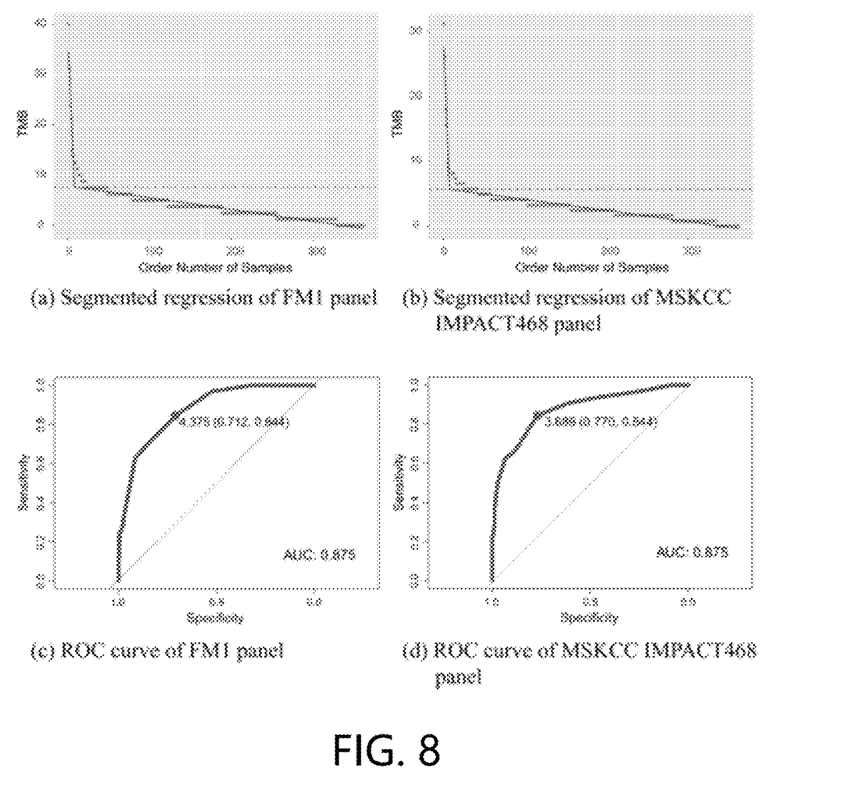
FIG. 8 is a schematic diagram of comparison between a classification accuracy and an AUC value of a classification model and a panel sequencing in one embodiment of the invention.

FIG. 8 is a schematic diagram of comparison between a classification accuracy and an AUC value of a classification model and a panel sequencing in one embodiment of the invention. As shown in FIG. 8, according to classification state determined by a WES-TMB inflection point value mentioned in the step S120, WES TMB classification accuracies predicted by the CNN model after training and the panel TMB are compared, and the classification accuracy and the AUC value of the FM1 panel of TMB are 0.807 and 0.875, respectively. Similarly, the classification accuracy and the AUC value of MSKCC IMPACT468 panel of the TMB are 0.778 and 0.875, respectively, which are far lower than corresponding scores predicted by the classification model in the invention.

Figure 9A:
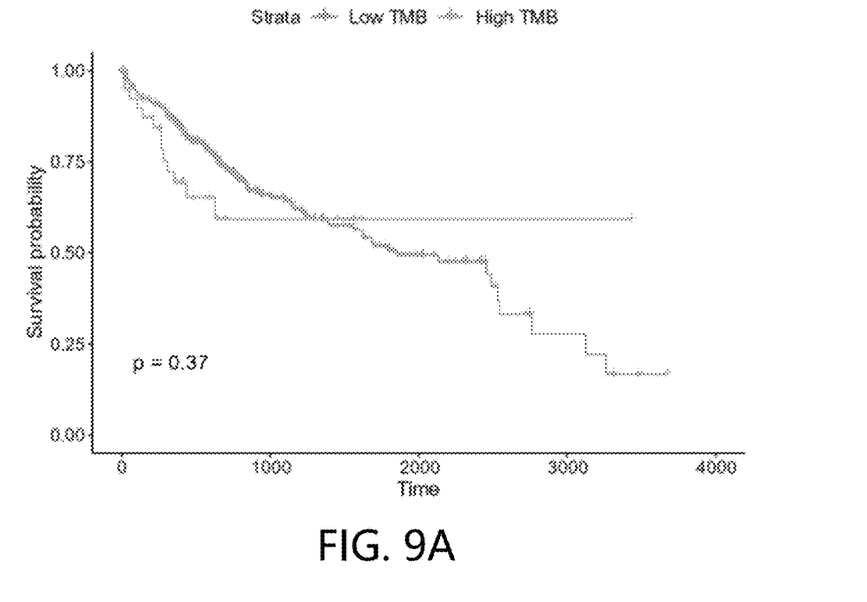
FIG. 9A is a schematic diagram of survival analysis based on MSKCC IMPACT468 panel.
Figure 9B:
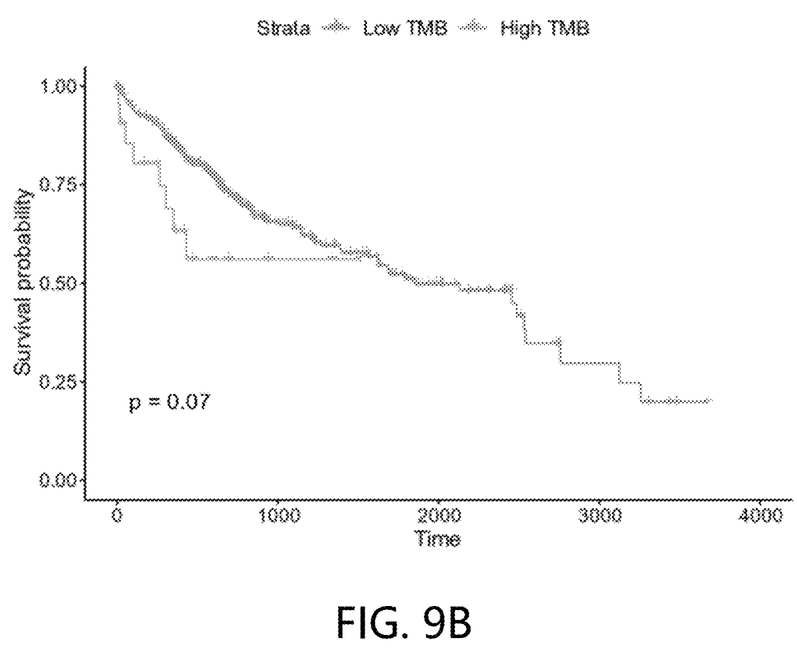
FIG. 9B is a schematic diagram of survival analysis based on FM1 panel.
Figure 9C:
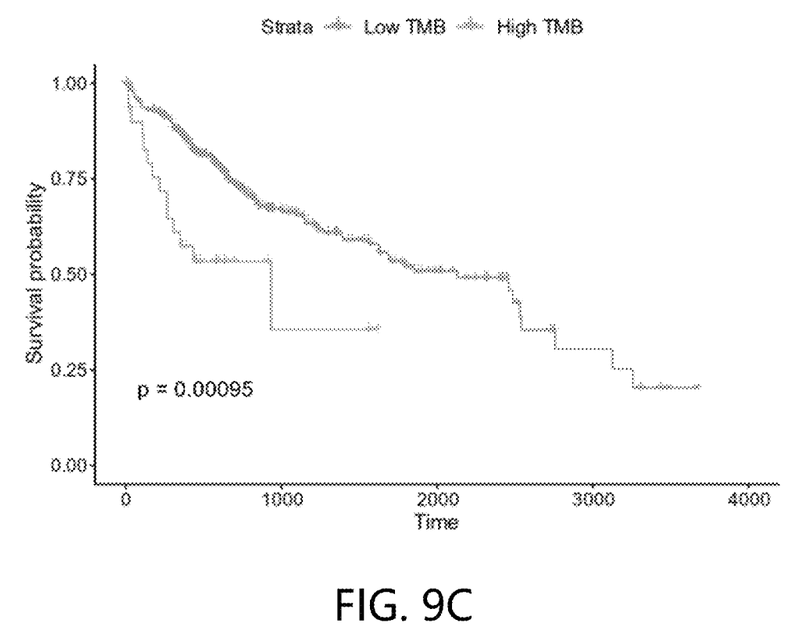
FIG. 9C is a schematic diagram of survival analysis predicted based on a CNN model according to the invention.

It is found from past research that a high TMB content in liver cancer is associated with bad prognosis, and survival predictive capabilities between TMB prediction classification based on the CNN model and TMB classification based on the panel are compared. Firstly, an inflection point of corresponding classification of the panel TMB is found using the segmented regression method. FIG. 9A is a schematic diagram of survival analysis based on MSKCC IMPACT468 panel, FIG. 9B is a schematic diagram of survival analysis based on FM1 panel, and FIG. 9C is a schematic diagram of survival analysis predicted based on CNN model according to the invention. As shown in FIGS. 9A, 9B and 9C, due to limit of testing regions, TMBs between adjacent patients are overfitted to the same value, in particular, in the patients with lower TMB, which directly reflects a low accuracy of the panel TMB. Analyses of survival curve show that survival time of high TMB group and low TMB group (mos=357 d vs 624 d, p=0.00095) predicted based on the CNN model has a significant difference, but no matter whether the high TMB group and the low TMB group use FM1 panel or MSKCC IMPAT468 panel, there is no significant difference. Obviously, the CNN model in the invention performs well, and is more advantageous for prognosis of the patients.

Experiments show that the classification model of the invention can better extract features of the liver cancer pathological image, thereby classifying high and low TMB levels of tumor tissues. Prediction of the model on survival probability of the patients is better than that of the TMB estimation method based on the panel.

(V) Relevant Pathological Explanations of the Classification Model

Figure 10:
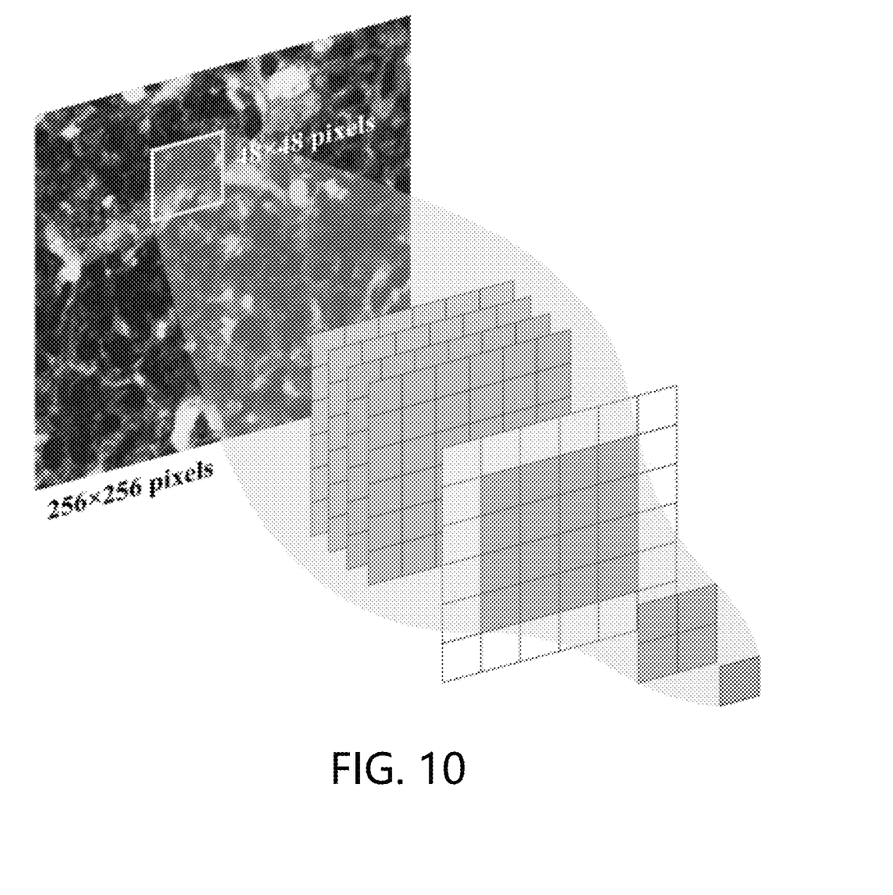
FIG. 10 is a schematic diagram of a receptive field of the classification model in one embodiment of the invention.

As for the pathological image, different receptive fields can obtain information of different feature scales, and small receptive fields can better acquire local information from the pathological image. In a HE slide under a 20× field of view, morphological feature of cancer cells belongs to local information, so small receptive fields can acquire better predicting results. FIG. 10 is a schematic diagram of a receptive field of the classification model in one embodiment of the invention. As shown in FIG. 10, it shows an exemplary region, and a field received by 48×48 pixels is projected onto an input image. In one 20× pathological image, the receptive field in such size includes about two cells. The receptive field in such size can assist the model in fully recognizing heterogeneity of liver cancer cells while avoiding interference of interstitial tissue that may occur in the pathological image.

Accumulation of gene mutations in normal cells causes generation of tumor cells. TMB is an index for reflecting a degree of gene mutations in the tumor cells, and can reflect pathogenesis of the tumors from a molecular level. Pathomorphological features of the tumor cells and microenvironment related cells have common inherent relation with inherent features of the genome of the tumor cells, thereby predicting TMB through the features of the pathological image. When observing a HE pathological section of liver cancer under a lens, it can be observed that as compared to a normal cell, a size and shape of the cancer cell are different, an internal structure is abnormal, and a karyoplasmic ratio is increased. Comparison of morphological features is shown in Table 4.

According to theory of the receptive field in deep learning, the receptive fields in different sizes can acquire information on different scales, and small receptive fields is better in acquiring local information. In a HE section under a 20× field of view, morphological features of cancer cells belong to local information, so better prediction effect can be obtained using small receptive fields.

TABLE 4

| Identification Points | Normal Cell | Cancer Cell |
|---|---|---|
| Cell Size | small in volume | large in volume |
| Cell Morphology | uniform | size nonuniform, morphology inconsistent, and having tumor giant cells |
| Nucleus Size | small | volume increased |
| Nucleus Morphology | circular or oval | volume increased, morphology inconsistent |
| Chromatin Feature | fine-grained | distribution irregular, coarse-grained |
| Nucleus Hyperchromatic | rare | common |
| Ratio of Nucleus to Cytoplasm | normal | increased |
| Nucleolus | small, morphology regular, and having a limited number | increased, morphology irregular, and having an increased number |
| Nucleus Mitotic Figure | rare | common, asymmetric, and multi-polarized |

INDUSTRIAL APPLICABILITY

The invention relates to a TMB classification method, system and a TMB analysis device based on a pathological image, comprising: performing TMB classification and marking and pre-processing on a known pathological image to construct a training set; training a convolutional neural network by means of the training set to construct a classification model; pre-processing a target pathological image of a target case to obtain a plurality of target image blocks; classifying the target image blocks by means of the classification model to acquire TMB classification results of image blocks of the target case; and acquiring a TMB classification result of an image of the target case by means of classification voting according to the TMB classification results of all the image blocks. The invention further relates to a TMB analysis device based on a pathological image. The TMB classification method of the invention has advantages of accuracy, low cost and fast speed, and has a significant value to research of tumors independent of samples except the pathological image.

What is claimed is:

1. A TMB classification method based on a pathological image, comprising:
performing TMB classification and marking and pre-processing on a known pathological image to construct a training set;
training a convolutional neural network by means of the training set to construct a classification model;
pre-processing a target pathological image of a target case to obtain a plurality of target image blocks;
classifying the target image blocks by means of the classification model to acquire TMB classification results of image blocks of the target case; and
acquiring a TMB classification result of an image of the target case by means of classification voting using the TMB classification results of all the image blocks.

2. The TMB classification method according to claim 1, wherein the step of pre-processing the target pathological image specifically comprises:
marking out a target tumor cell region of the target pathological image;
cutting out target local images from the target pathological image according to the target tumor cell region; and
performing a sliding window segmentation of the target local images, and performing a color inversion of a target intermediate image block obtained by segmentation to obtain the plurality of target image blocks.

3. The TMB classification method according to claim 1, wherein the step of constructing the training set specifically comprises:
classifying the known pathological image into a plurality of types according to TMB through at least one classification threshold;
marking out all known tumor cell regions of the known pathological image;
cutting out a known local image from the known pathological image according to the known tumor cell regions;
performing a sliding window segmentation of the known local image, and performing a color inversion of an intermediate image block obtained by segmentation to obtain a plurality of training image blocks; and
randomly dividing all the training image blocks to construct training subsets and testing subsets of the training set.

4. The TMB classification method according to claim 1, wherein the convolutional neural network comprises four pairs of convolutional layers and the maximum pooling layer, one layer of first fully-connected layer, and one layer of second fully-connected layer sequentially; all convolutional layers and the first fully-connected layer use ReLU activation function, and the second fully-connected layer uses Sigmoid activation function;
obtaining a plurality of preselected receptive fields by changing a fine grain of convolution kernels of respective convolutional layers of the convolutional neural network, constructing a plurality of corresponding preselected classification models, and acquiring an accuracy and an AUC value of the preselected classification models to use the preselected classification model having the maximum accuracy and the maximum AUC value as the classification model, and the preselected receptive field corresponding to the classification model as an optimal receptive field.

5. A non-tangible computer readable storage medium stored with an executable instruction for executing the TMB classification method based on a pathological image according to claim 1.

6. A TMB analysis device based on a pathological image, comprising a processor and the readable storage medium according to claim 5, the processor calling an executable instruction in the readable storage medium to analyze a target pathological image, and acquire a target classification result of the target pathological image.

7. A TMB classification system based on a pathological image, comprising:
a training set construction module for performing TMB classification and marking and pre-processing on a known pathological image to construct a training set;
a classification model construction module for training a convolutional neural network by means of the training set to construct a classification model;
a target image pre-processing module for pre-processing a target pathological image of a target case to obtain a plurality of target image blocks;
an image block classification module for classifying the target image blocks by means of the classification model to acquire TMB classification results of image blocks of the target case; and
an image classification module for acquiring a TMB classification result of an image of the target case by means of classification voting using the TMB classification results of all the image blocks.

8. The TMB classification system according to claim 7, wherein the target image pre-processing module specifically comprises:
marking out a target tumor cell region of the target pathological image; cutting out target local images from the target pathological image according to the target tumor cell region; and performing a sliding window segmentation of the target local images, and performing a color inversion of a target intermediate image block obtained by segmentation to obtain the plurality of target image blocks.

9. The TMB classification system according to claim 7, wherein the training set construction module comprises:
a TMB marking module for classifying the known pathological image into a plurality of types according to TMB through at least one classification threshold;
a local region cutting-out module for marking out all known tumor cell regions of the known pathological image, and cutting out a known local image from the known pathological image according to the known tumor cell regions;
a training image block segmentation module for performing a sliding window segmentation of the known local image, and performing a color inversion of an intermediate image block obtained by segmentation to obtain a plurality of training image blocks; and
a training set dividing module for randomly dividing all the training image blocks to construct training subsets and testing subsets of the training set.

10. The TMB classification system according to claim 7, wherein the convolutional neural network comprises four pairs of convolutional layers and the maximum pooling layer, one layer of first fully-connected layer, and one layer of second fully-connected layer sequentially; all convolutional layers and the first fully-connected layer use ReLU activation function, and the second fully-connected layer uses Sigmoid activation function;

obtaining a plurality of preselected receptive fields by changing a fine grain of convolution kernels of respective convolutional layers of the convolutional neural network, constructing a plurality of corresponding preselected classification models, and acquiring an accuracy and an AUC value of the preselected classification models to use the preselected classification model having the maximum accuracy and the maximum AUC value as the classification model, and the preselected receptive field corresponding to the classification model as an optimal receptive field.

* * * * *